United States Patent [19]

Kawaguchi et al.

[11] Patent Number: 4,914,036
[45] Date of Patent: Apr. 3, 1990

[54] METHOD AND APPARATUS FOR SIMULTANEOUSLY ANALYZING VANILLYLMANDELIC ACID, HOMOVANILLIC ACID AND CREATININE

[75] Inventors: Seiji Kawaguchi, Yokohama; Hiroaki Takahashi, Sagamihara; Yuji Saito, Yokohama, all of Japan

[73] Assignee: Tosoh Corporation, Shin-nanyo, Japan

[21] Appl. No.: 163,318

[22] Filed: Mar. 2, 1988

[30] Foreign Application Priority Data

Mar. 2, 1987 [JP] Japan .................................. 62-45297

[51] Int. Cl.⁴ ............................................. G01N 33/00
[52] U.S. Cl. ........................................ 436/98; 436/811
[58] Field of Search ................ 435/7; 422/70; 436/98, 436/811

[56] References Cited

U.S. PATENT DOCUMENTS

| | | | |
|---|---|---|---|
| 4,319,883 | 3/1982 | Imai et al. ............................ | 436/131 |
| 4,446,105 | 5/1984 | Dinsmore et al. .................... | 422/70 |
| 4,687,733 | 8/1987 | Trewyn et al. ......................... | 435/7 |

OTHER PUBLICATIONS

"Liquid-Chromatographic Assay for Urinary Homovanillic Acid, with Fluorescent Detection", *Clinical Chem.*, vol. 27, No. 2, 1987.
"Simple High-Performance Liquid Chromatographic . . . ", Journal of Chromatography, 226, published in 1981.
"Simple Method for the Determination . . . ", Journal of Chromatography, 227, published in 1982.

*Primary Examiner*—Barry S. Richman
*Assistant Examiner*—T. J. Wallen
*Attorney, Agent, or Firm*—Cushman, Darby & Cushman

[57] ABSTRACT

A method for analyzing vanillylmandelic acid, homovanillic acid and creatinine by fast liquid chromatography, which comprises a step of introducing a test solution containing vanillylmandelic acid, homovanillic acid and creatinine to a cation exchange resin column and separating creatinine from vanillylmandelic acid and homovanillic acid; a step of separating by a separation column vanillylmandelic acid and homovanillic acid in the test solution from which creatinine has been separated, and a step of detecting each component.

2 Claims, 6 Drawing Sheets

METHOD AND APPARATUS FOR SIMULTANEOUSLY ANALYZING VANILLYLMANDELIC ACID, HOMOVANILLIC ACID AND CREATININE

BACKGROUND OF THE INVENTION

1. Field of the Invention

Neuroblast tumor (hereinafter referred to simply as NB) is a malignant tumor specific to infancy and curable only when discovered at an early stage. Therefore, early discovery and diagnosis are desired. In the case of true disease, vanillylmandelic acid (hereinafter referred to simply as VMA) and homovanillic acid (hereinafter referred to simply as HVA) as metabolic products of catechol amine are discharged into urine in substantial amounts. Accordingly, it is possible to diagnose NB in a high probability by measuring these two components in urine. In Japan, NB mass screening for children has been started since January 1985 at a governmental level.

The present invention relates to a method for simultaneously analyzing VMA, HVA and creatinine (hereinafter referred to simply as CRN) in a test solution quickly and accurately with high sensitivity for such NB mass screening, and to an apparatus useful for such a method.

2. DISCUSSION OF BACKGROUND

In recent years, it has been common to use fast liquid chromatography for the measurement of VMA and HVA. In this method, the separation is conducted by reversed phase chromatography or anion exchange chromatography and the detection is conducted by a ultraviolet absorption measuring method (A. Yoshida, et al, J. Chromatogr., 227,162 (1982)), an electrochemical measuring method (M. H. Joseph, et al, J. Chromatogr., 226,361 (1981)) or a fluorescence measuring method (T. G. Rosano, et al, Clin. Chem. 27,228 (1981)).

However, in the test solution, there exist acidic components such as uric acid and other organic acids and basic components such as polyamines, in addition to the object components. These inclusions are likely to interfere with the determination. Accordingly, it used to be difficult to directly inject the test sample, and it used to be required to have some pretreatment conducted. For such pretreatment, it has been common to employ a method wherein urine or urine-absorbed filter paper is extracted with ethyl acetate or with a buffer solution. However, each of such methods involves manual operation and thus has drawbacks such that not only the operation is cumbersome but also the recovery rates are likely to be irregular, and it is not possible to completely eliminate the influence of inclusions.

On the other hand, in the determination of the quantity of a certain component in urine, it is common to adopt a creatinine ratio (CRN ratio) as a means for correction against the change of the amount of urine. Likewise, in the quantitative determination of VMA and HVA, it is necessary to preliminarily measure the CRN concentration in urine. In the conventional methods, the measurement of CRN was conducted by a method entirely independent from the system for the measurement of VMA and HVA, whereby the analysis of data was not only complex but also time-consuming. Therefore, the simplification has been desired.

As mentioned above, the conventional methods require a cumbersome pretreatment operation such as solvent extraction of VMA and HVA. Further, since the CRN analysis used to be impossible in a single series of measuring system, it took a long period of time for the overall analysis.

SUMMARY OF THE INVENTION

It is an object of the present invention to provide a method for analyzing VMA, HVA and CRN faster and more accurately with higher sensitivity than such conventional methods, and to provide an apparatus for analysis to be used for such a method.

The present invention provides a method for analyzing vanillylmandelic acid, homovanillic acid and creatinine by fast liquid chromatography, which comprises a step of introducing a test solution containing vanillylmandelic acid, homovanillic acid and creatinine to a cation exchange resin column and separating creatinine from vanillylmandelic acid and homovanillic acid; a step of separating by a separation column vanillylmandelic acid and homovanillic acid in the test solution from which creatinine has been separated; and a step of detecting each component.

Further, the present invention provides an apparatus for analyzing vanillylmandelic acid, homovanillic acid and creatinine by fast liquid chromatography, which comprises a cation exchange resin column (7A) for separating creatinine from vanillylmandelic acid and homovanillic acid in a test solution, an anion exchange column (7B) for partially fractionating vanillylmandelic acid and homovanillic acid from other acidic components, a separation column (9) for separating vanillylmandelic acid and homovanillic acid, a flow path switching valve (8A) connected to the cation exchange column (7A) to change the path of eluent, a flow path switching valve (8B) connected to the anion exchange resin column (7B) and the separation column (9), and a detector (10, 11) for detecting each component, wherein the cation exchange resin column (7A) and the anion exchange resin column (7B), and the anion exchange resin column (7B) and the separation column (9) are connected in series, respectively.

DETAILED DESCRIPTION OF THE INVENTION

Now, the present invention will be described in detail.

The cation exchange resin column for separating CRN from VMA and HVA according to the present invention is preferably a column packed with a strong acid type cation exchange resin. VMA, HVA and other acidic components have no interaction with such a column, whereas CRN and other basic components have an interaction therewith. Accordingly, VMA and HVA are eluted first, whereby they are separated from CRN.

Then, the test solution from which CRN has been separated, is led to the separation column for separating VMA and HVA. As such a separation column, a reversed phase chromatography column or an anion exchange resin column may be employed. It is preferred to employ the reversed phase chromatography column.

In order to maintain the useful life of the searation column, it is effective that prior to the separation of VMA and HVA, partial fractionation is conducted by an anion exchange resin column, preferably by a weak base type anion exchange resin column, to partially fractionate VMA and HVA from other acidic components so that unnecessary acidic components other than VMA and HVA will not be introduced to the separation column. Here, the partial fractionation means that VMA and HVA may not necessarily completely be separated from other acidic components.

Various methods may be employed for the detection of the respective components for the present invention. For the detection of CRN, it is preferred to employ an ultraviolet absorption measuring method. Whereas, for the detection of VMA and HVA, an ultraviolet absorption measuring method, an electrochemical measuring method or a fluorescence measuring method may suitably be selected. However, from the viewpoint of the sensitivity and selectivity, the electrochemical measuring method or the fluorescence measuring method is preferred.

As the eluent to be used in each separation step of the present invention, there may be employed a phosphoric acid buffer solution containing acetonitrile, which is commonly employed.

By adopting the above-mentioned method, not only VMA and HVA but also CRN can be separated and analyzed simultaneously by a single fast liquid chromatography apparatus by using a single test sample solution.

The analytical method of the present invention and the analytical apparatus to carry out the method will be further described with reference to the drawings.

Figure 1:
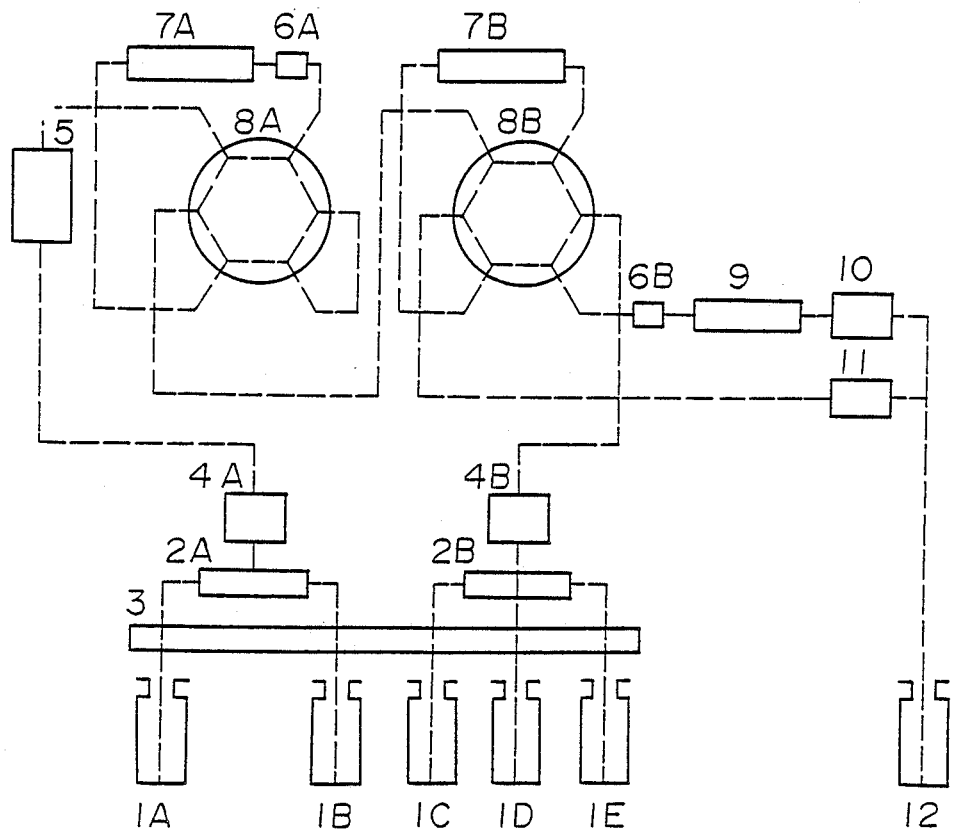
FIG. 1 is a diagrammatic view illustrating an embodiment of the apparatus useful for analysis according to the method of the present invention.

FIG. 1 shows an embodiment of the method and apparatus of the present invention.

This analytical apparatus comprises a cation exchange resin column (7A) for separating CRN from VMA and HVA in the test solution, an anion exchange resin column (7B) for partially fractionating VMA and HVA from other acidic components, a separation column (9) for separating VMA and HVA, a valve (8A) connected to the cation exchange resin column (7A), a valve (8B) connected to the anion exchange resin column (7B) and the separation column (9), a detector (10) for detecting VMA and HVA and a detector (11) for detecting CRN, wherein said cation exchange resin column (7A) and said anion exchange resin column (7B), and said anion exchange resin column (7B) and said separation column (9) are connected in series, respectively. Further, the apparatus includes eluent tanks (1A-1E), eluent switching valves (2A, 2B), eluent supplying pumps (4A, 4B), a degasser (3), a sample supplying device (5), prefilters (6A, 6B) and a waste solution tank (12).

The test solution which is a sample, is led by the eluent (1A) to the cation exchange resin column (7A), where VMA, HVA and other acid components eluting first will be separated from CRN and other basic components eluting later. The eluent from which CRN has been separated, is then led to the anion exchange resin column, where VMA and HVA are partially fractionated from other acidic components. VMA and HVA eluting first through the anion exchange resin column (7B) are then led to a separation column (9) by an eluent (1C, 1D) by switching the valve (8B). Here, VMA and HVA are separated. CRN eluting later from the cation exchange resin column (7A) is led to a detector (11) by the valve operation and thereby detected. On the other hand, VMA and HVA eluting from the separation column (9) are likewise detected by a detector (10). After the completion of the detection of the respective components, the respective eluents (1B, 1E) are supplied to wash the eluent paths. After completion of this initial operation, the analysis may be repeated by introducing a sample again.

The combination or sequential order of the cation exchange resin column (7A), the anion exchange resin column (7B) and the separation column (9) may be different from the above, so long as the cation exchange resin column (7A) and the anion exchange resin column (7B), and the anion exchange resin column (7B) and the separation column (9) are connected in series, respectively.

It is advantageous to control such an analytical apparatus by a computer from the viewpoint of the analytical operation and saving of the time for the analysis.

In FIG. 1, a six way valve is used as the valve (8A). However, the valve (8A) may be a four way valve.

For the detection of CRN, it is possible to use a third pump for the cation exchange resin column (7A). For the simplification, however, the analytical apparatus shown in FIG. 1 has only two supplying pumps.

Now, the present invention will be described in further detail with reference to an Example. However, it should be understood that the present invention is by no means restricted by such a specific Example.

EXAMPLE

The analytical apparatus used for the analysis was as shown in FIG. 1, wherein as the cation exchange resin column (7A), a strong acid-type TSK GEL SP-2 SW (4.6 I.D. x 120 mm, manufactured by TOSOH CORPORATION) was used, as the anion exchange resin column (7B), a weak base-type TSK GEL DEAE-2 SW (4.6 I.D. x 120 mm, manufactured by TOSOH CORPORATION) was used, and as the separation column (9), TSK GEL ODS-80 TM (4.6 I.D. x 150 mm, manufactured by TOSOH CORPORATION) for reversed phase chromatography was used. For the detection of VMA and HVA, a fluorescence detector was used as the detector (10), and the wavelength for measurement was 280 nm for $\lambda EX$ and 320 nm for $\lambda EM$. For the detection of CRN, an ultraviolet absorption detector was used as the detector (11), and the wavelength ($\lambda$) for the measurement was 240 nm.

With respect to various eluents, a 50 mM phosphoric acid buffer solution (pH 4.8) containing 10% of acetonitrile was used as the eluent (1A), a 50 mM phosphoric acid buffer solution (pH 4.8) containing 10% of acetonitrile and 300 mM sodium chloride was used as the eluent (1B), a 50 mM phosphoric acid buffer solution (pH 5.2) was used as the eluent (1C), a 50 mM phosphoric acid buffer solution (pH 5.2) containing 6% of acetonitrile was used as the eluent (1D) and a 50 mM phosphoric acid buffer solution (pH 5.2) containing 50% of acetonitrile was used as the eluent (1E).

As the test sample solutions, a standard sample containing 4 ng of each of VMA and HVA and 400 ng of CRN, and urine discharged by a healthy man by single urination, were used.

The operational sequence for carrying out the analytical operation will be described with reference to FIG. 2.

Figure 2A:
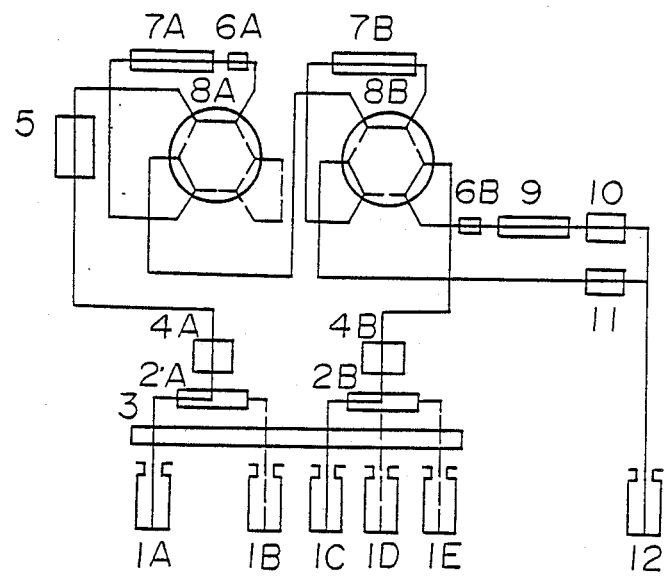
FIG. 2 illustrates the sequential operation of the apparatus for analysis in the Example.
Figure 2B:
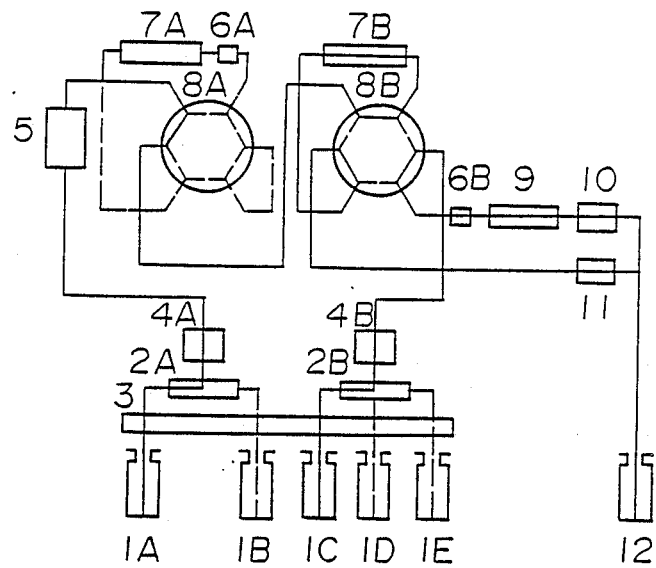
Figure 2C:
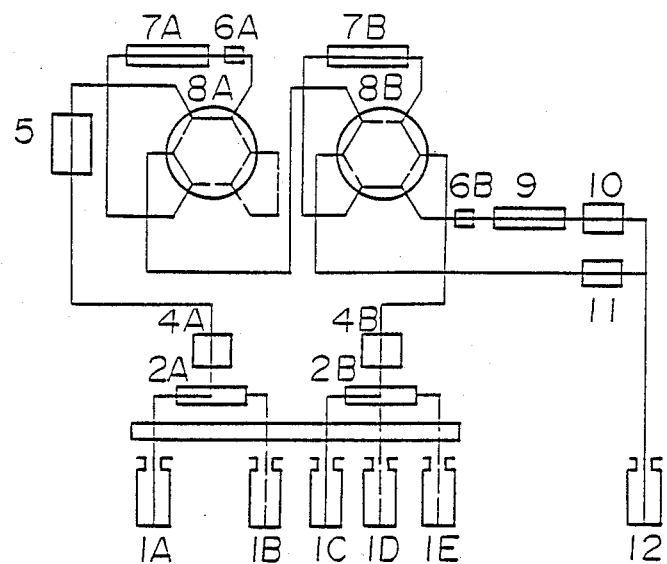
Figure 2D:
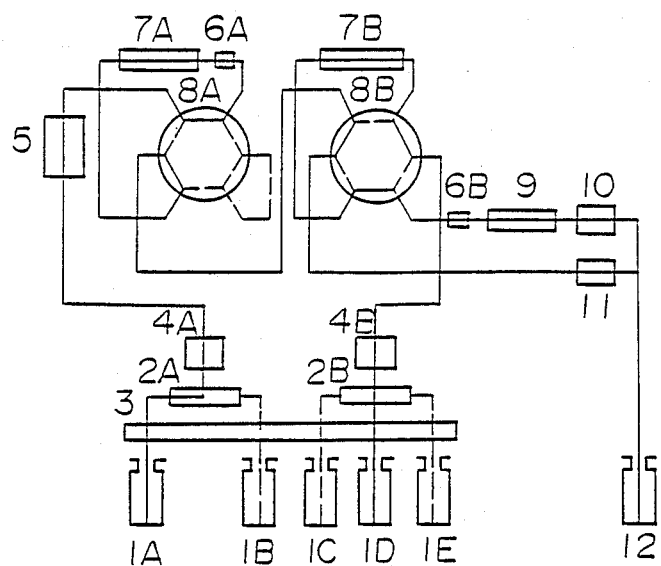
Figure 2E:
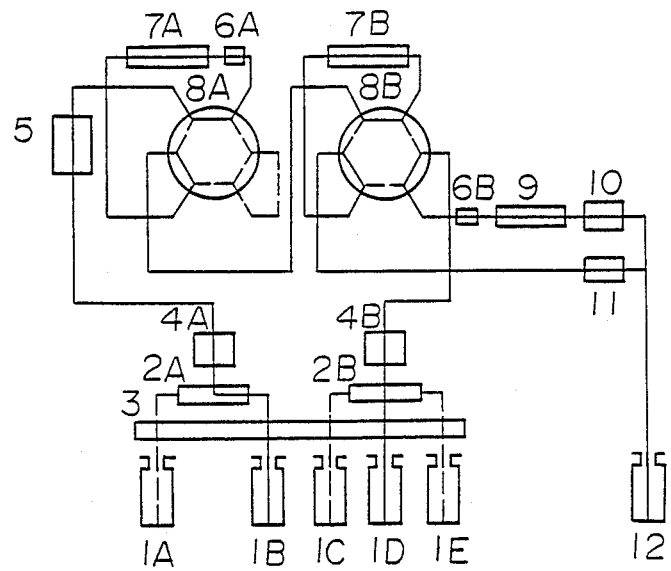
Figure 2F:
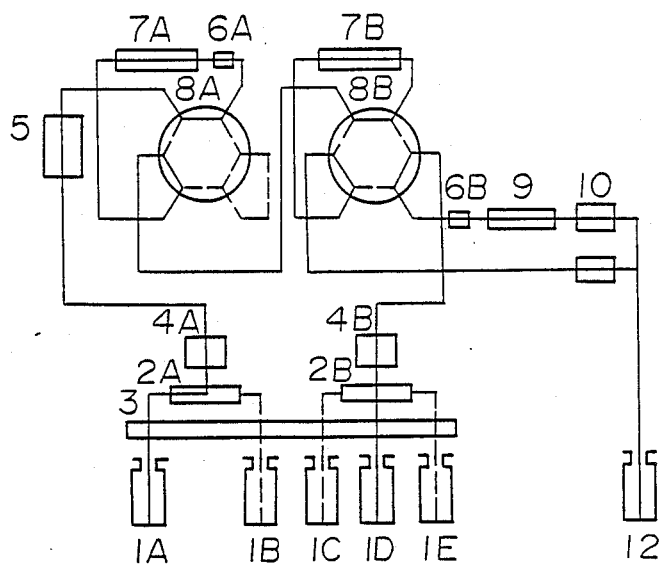
Figure 2G:
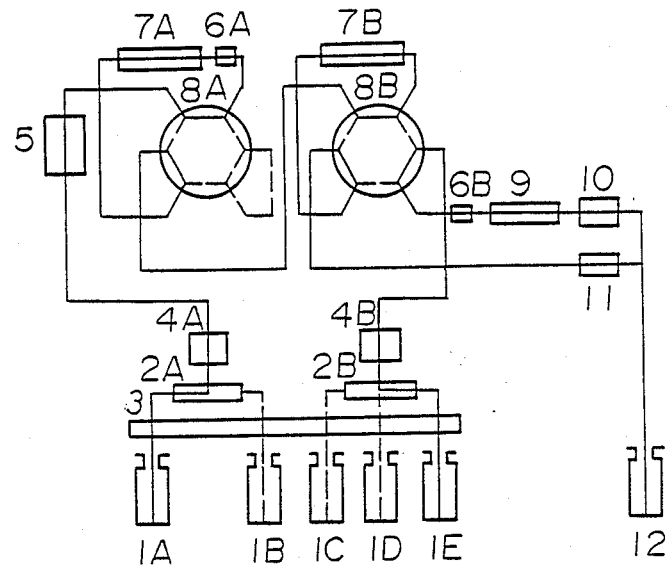
Figure 2H:
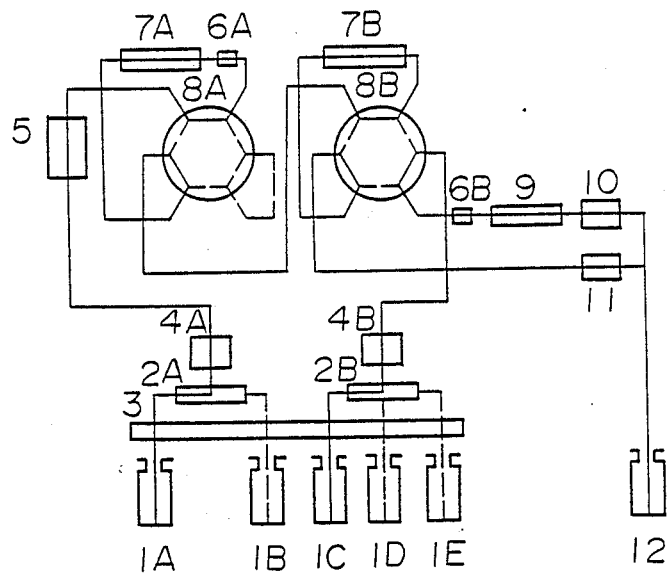

Firstly, the paths for eluents are set for the initial state. As shown in FIG. 2(a), the eluent (1C) is filled in the detector (10) through the separation column (9). On the other hand, the eluent (1A) is filled in the other path. The sample is introduced from the sample supplying device (5) to the eluent path, and VMA, HVA and CRN are led to the cation exchange resin column (7A). Here, when VMA and HVA eluting first are introduced to the anion exchange resin column (7B), the valve (8A) is switched as shown in FIG. 2(b) to temporarily stop the supply to the cation exchange resin column (7A) and stop the elution of CRN. When the partial fractionation in the anion exchange resin column (7B) with the eluent (1A) has been completed and VMA and HVA have eluted, the valves (8A, 8B) are switched as shown in FIG. 2(c), whereupon VMA and HVA are led by the eluent (1C) to the separation column (9), while CRN is led to the detector (10) by the eluent (1A) and thereby detected. In the separation column (9), VMA and HVA are separated by the eluent (1C) and then by the eluent (1D) as shown in FIG. 2(d). Then, the valve (8B) is switched as shown in FIG. 2(e) not to introduce other acidic components partially fractionated in the anion exchange resin column (7B) to the separation column (9). At the same time, the eluent (1B) is supplied to the path to which the eluent (1A) has been supplied, to wash the path, and then the valve is switched as shown in FIG. 2(f) to supply the eluent (1A) for the initial state. Meantime, VMA and HVA are completely separated and detected by the detector. After the separation and detection, the path of the separation column (9) is washed by the eluent (1E) as shown in FIG. 2(g), and then finally switched to the eluent (1C) as shown in FIG. 2(h) for the initial state.

The analyses of the standard sample and the urine test sample were conducted by controlling the above analytical operation by a computer. The eluents flowing through the respective columns during each step and the operational step of each valve are shown in Table 1 together with the operational sequence of FIG. 2. One cycle for the introduction of a sample was 15 minutes.

(1) In the analyses of VMA and HVA and CRN, a cumbersome operation such as a pretreatment operation for the extraction with ethyl acetate, is not required;
(2) VMA, HVA and CRN can be simultaneously analyzed, whereby the CRN ratio important as an index for the NB diagnosis can readily and accurately be measured; and
(3) No special or complex operation is required for the separation of each component, and the analyses can be completed in a short period of time. The operation can be readily controlled by a computer, whereby manpower can be saved.

What is claimed is:
1. A method for analyzing a test solution comprising vanillylmandelic acid, homovanillic acid and creatinine by fast liquid chromatography, which comprises:
a step of introducing a first inlet stream comprising a test solution containing vanillylmandelic acid, homovanillic acid and creatinine and a second inlet stream comprising a first eluent to a cation exchange resin column, separating creatinine from vanillylmandelic acid and homovanillic acid using said first eluent, and removing from said cation exchange resin column a first outlet stream comprising vanillylmandelic acid and homovanillic acid and a second outlet stream comprising creatinine, wherein at least one of said first and second outlet streams further comprises said first eluent;
a step of introducing said first outlet stream from said cation exchange resin column and a second eluent stream into a separation column, separating vanillylmandelic acid and homovanillic acid using said second eluent, and removing from said separation column a third outlet stream comprising vanillylmandelic acid and a fourth outlet stream comprising homovanillic acid, wherein at least one of said third and fourth outlet streams further comprises said second eluent; and
a step of detecting each component in said second, third and fourth outlet streams.

TABLE 1

| Time (min.) | Column (7A) | Column (7B) | Column (9) | Column (8A) | Column (8B) | FIG. 2 |
|---|---|---|---|---|---|---|
| 0.0–2.2 | 1A | 1A | 1C | OFF | OFF | a |
| 2.2–6.5 | (1A) | 1A | 1C | ON | OFF | b |
| 6.5–9.0 | 1A | 1C | 1C | OFF | ON | c |
| 9.0–10.0 | 1A | 1D | 1D | OFF | ON | d |
| 10.0–10.5 | 1B | 1B | 1D | OFF | OFF | e |
| 10.5–14.0 | 1A | 1A | 1D | OFF | OFF | f |
| 14.0–14.5 | 1A | 1A | 1E | OFF | OFF | g |
| 14.5–15.0 | 1A | 1A | 1C | OFF | OFF | h |

Figure 3:
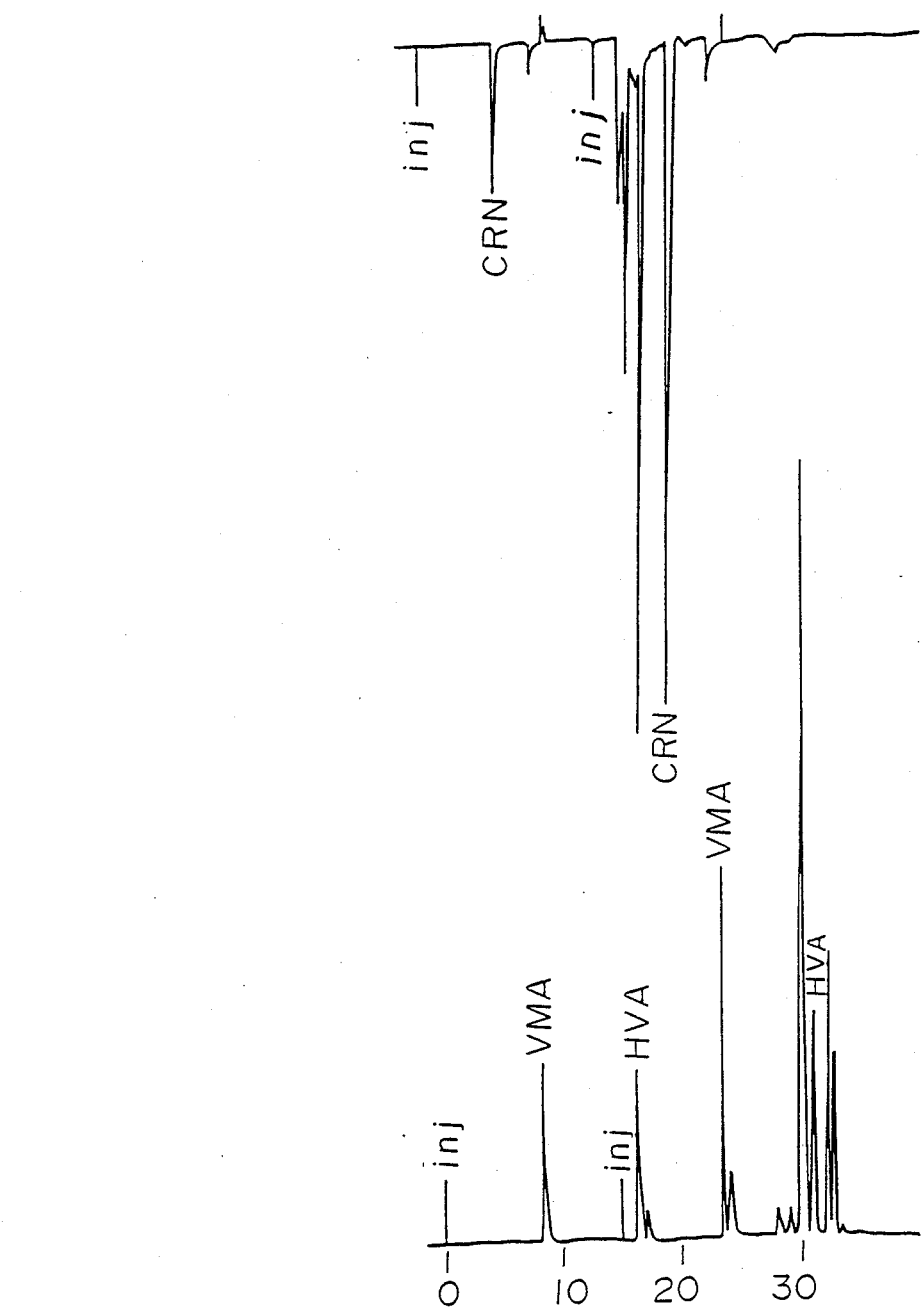
FIG. 3 is a chromatogram as an example of the analysis of a standard sample and a test sample.

The chromatogram thus obtained is shown in FIG. 3.
As is apparent from the foregoing description, the present invention provides the following advantageous:

2. A method of detecting neuroblastoma by analyzing a test solution according to the method of claim 1 and comparing the amount of vanillylmandelic acid and homovanillic acid to those of a normal subject.

* * * * *